United States Patent
Kim et al.

(10) Patent No.: US 7,045,300 B2
(45) Date of Patent: May 16, 2006

(54) **LECTIN PROTEIN PREPARED FROM *MAACKIA FAURIEI*, PROCESS FOR PREPARING THE SAME AND THE USE THEREOF**

(76) Inventors: Ha-Hyung Kim, Ma-1008 Bangbaesamho Apt., 725 Bangbae-dong, Seocho-ku, 137-060 Seoul (KR); Bum-Soo Kim, 208-202 Woosung Apt., 105 Sadang-dong, Kongjak-ku, 156-773 Seoul (KR); Kwang-Hoon Kong, 102-1307 Hyundai Apt., 66 Gyesan-dong, Gyeyang-ku, 407-050 Incheon-shi, Kyonggi-do (KR)

( * ) Notice: Subject to any disclaimer, the term of this patent is extended or adjusted under 35 U.S.C. 154(b) by 4 days.

(21) Appl. No.: 10/478,370

(22) PCT Filed: May 14, 2002

(86) PCT No.: PCT/KR02/00894

§ 371 (c)(1),
(2), (4) Date: Jun. 8, 2004

(87) PCT Pub. No.: WO02/094869

PCT Pub. Date: Nov. 28, 2002

(65) Prior Publication Data

US 2005/0084903 A1    Apr. 21, 2005

(30) Foreign Application Priority Data

May 22, 2001    (KR)  ............... 2001-27943

(51) Int. Cl.
  *G01N 33/53*   (2006.01)
  *A61K 38/16*   (2006.01)
  *C07K 14/415*  (2006.01)

(52) U.S. Cl. ............... 435/7.1; 514/8; 530/379

(58) Field of Classification Search ............... 530/396, 530/350, 395, 379; 435/7.1; 514/8
See application file for complete search history.

(56) References Cited

OTHER PUBLICATIONS

Van Damme, J.M., et al. 1997. Isolation, characterization and molecular cloning of the bark lectins from *Maackia amurensis*. Glycoconjugate Journal. 14: 449-456.*

* cited by examiner

*Primary Examiner*—Karen Cochrane Carlson
*Assistant Examiner*—Marsha Tsay
(74) *Attorney, Agent, or Firm*—Thompson Hine LLP

(57) ABSTRACT

The present invention relates to a lectin protein, designated MFA isolated and purified from the bark of the Korean legume *Maackia fauriei*, process for preparing the same and the use thereof. This protein can be used as reagents in the study of carbohydrate binding proteins as well as to examine the distribution of N-acetylneuraminic acid in cancer cells owing to its capability that specifically recognizes N-acetylneuraminic acid which plays important structural and functional roles in the expressions of various cells or oligosaccharide terminal residue of glycoconjugates, and, in addition, used as an anti-cancer drug in view of its anti-proliferation effect against various cancers such as breast cancer, melanoma, hepatoma, etc.

7 Claims, 6 Drawing Sheets

● ;Absorbance at 280nm, ○ ;Hemagglutination titer

SEQUENCE LISTING

<160> NUMBER OF SEQ ID NOS: 1

<210> SEQ ID NO 1
<211> LENGTH: 20
<212> TYPE: PRT
<213> ORGANISM: Maackia fauriei

<400> SEQUENCE: 1

```
Ser Asp Glu Leu Ser Phe Asn Ile Asn Asn Phe Val Pro Asn Gln Ala
1               5                   10                  15

Asp Leu Leu Phe
            20
```

US 7,045,300 B2

LECTIN PROTEIN PREPARED FROM *MAACKIA FAURIEI*, PROCESS FOR PREPARING THE SAME AND THE USE THEREOF

CROSS REFERENCE TO RELATED APPLICATIONS

This application is filed under the provisions of 35 U.S.C. §371 of International Application PCT/KR02100894 filed May 14, 2002, claiming priority to KR2001-27943 filed May 22, 2001.

TECHNICAL FIELD

The present invention relates to a lectin protein isolated from the bark of the Korean legume *Maackia fauriei* in the family *Leguminosae*, a process for preparing the same and the use thereof. More specifically, the present invention relates to a lectin MFA (*Maackia fauriei* agglutinin) that is a protein component isolated from the bark of the Korean legume *Maackia fauriei* and specifically binds to N-acetylneuraminic acid, a process for isolating and purifying the same, and the various uses of the MFA based on its biological activities.

BACKGROUND ART

Recently, as the techniques for elucidating and controlling the structure and function of a biological material have been rapidly developed in the genetic engineering or protein engineering, the understanding of vital phenomenon is progressed at the gene and protein levels, and at the same time, carbohydrates such as oligosaccharides in the living body are also considered as an essential subject in elucidating the regulatory mechanism of the living body. In order to advance the related researches, the studies on the effect of oligosaccharides on the structure and function of the living body and on the effect on intercellular communication, etc. shall be systemically carried out.

Oligosaccharides, an essential component constituting the living body play essential roles in maintaining biological activities such as cellular adhesion, intercellular communication, and morphogenesis of individual tissue by forming a complex molecule such as glycoproteins or glycolipids conjugated with proteins or lipids.

The functions of oligosaccharides known hitherto are mainly classified into three kinds: First, oligosaccharides bind to other proteins, thus playing an important role in specific recognition of cells by the interaction. The next is the case where oligosaccharide bound to protein itself significantly modifies the inherent function of the protein. The example thereof includes N-CAM which is the cellular adhesive molecule of oligosaccharide specifically expressing in the brain such as polysialic acid. Third, most of proteins are glycoproteins in which oligosaccharide is bound to the protein via Asn or Ser/Thr of the protein itself by which activate functions of the protein. That is, oligosaccharide is considered to be an important material which results in change of function by itself or by the combination with other biological materials.

Intercellular recognition occurs by way of carbohydrates on the cell membrane surface, and in order to mediate this process molecules specifically recognizing the carbohydrates should exist on the cell membrane surface. For example, a carbohydrate-binding protein such as lectin is necessary on the cell membrane surface.

Korean legume *Maackia fauriei*, which belongs to the family *Leguminosae* is a deciduous forest tree and a specialty plant of Korea and is distributed in large amounts throughout the height 1,100–1800 m of the Cheju island in Korea. However, the biochemical researches thereon are very poor.

DISCLOSURE OF INVENTION

The present inventors have conducted extensive studies in order to characterize and test biological activity of the protein, lectin MFA the presence of which has not been known hitherto by isolating it from the bark of the Korean legume *Maackia Fauriei* by a method which will be described below, and as a result found that it has various beneficial biochemical characteristics such as a specific binding to N-acetylneuraminic acid, and thus can be used as reagents in the study of carbohydrate-binding protein and an anti-proliferation agent against cancer cells, etc, and completed the present invention.

It is therefore an object of the present invention to provide a lectin protein MFA which was isolated from the bark of the Korean legume *Maackia fauriei* and is a kind of proteins which specifically recognize to N-acetylneuraminic acid.

It is another object of the present invention to provide a process for preparing the lectin MFA.

It is further object of the present invention to provide diagnostics for detecting a disease in which the structure of carbohydrates within the cells contains N-acetylneuraminic acid and its distribution is changed due to invasion of diseases, which comprises the lectin MFA.

It is still another object of the present invention to provide a use of the lectin MFA as an anti-cancer drug with an anti-proliferation effect against cancer cells.

It is still further object of the present invention to provide uses of the lectin MFA in the research material of immunobiochemistry or in agglutination of cancer cells.

BRIEF DESCRIPTION OF THE DRAWINGS

Further objects and advantages of the invention can be more fully understood from the following detailed description taken in conjunction with the accompanying drawings in which.

BEST MODE FOR CARRYING OUT THE INVENTION

Figure 1:
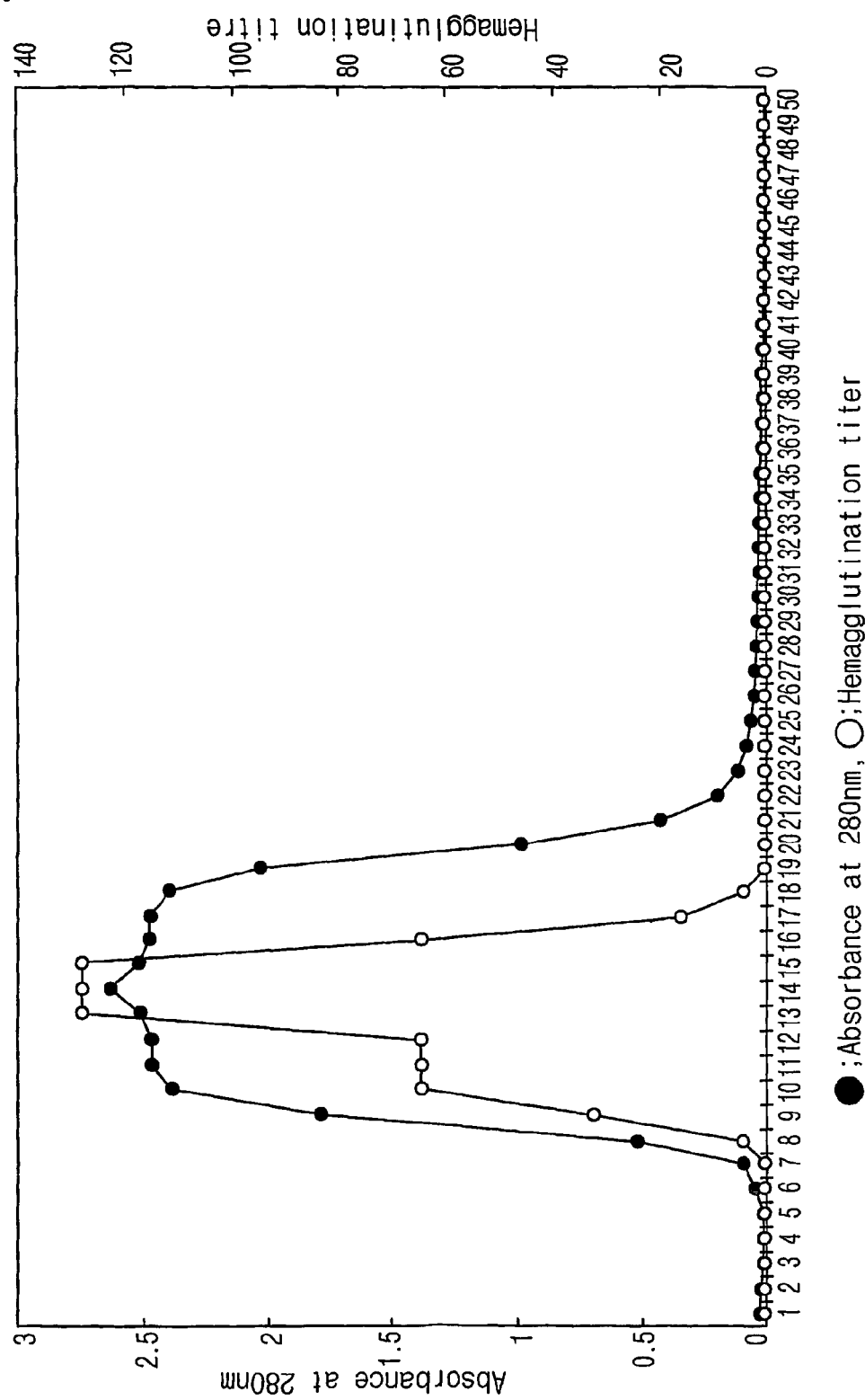
FIG. 1 is a graph showing a UV (280 nm) spectroscopic chromatogram and the hemagglutination response by a Sepharose CL-6B column of the extract containing the lectin MFA prepared by the present invention.

Hereinafter, the present invention will be described in further detail.

Lectin, which is a protein selectively binding to carbohydrates, has originally been discovered from plants, microorganisms, virus, invertebrates or vertebrates and widely used as a material for various disease-related researches. Lectin has various functions: it has been known to agglutinate erythrocytes to sediment them, and has been used in determining blood type. In addition, it has recently been known to have a function of specifically agglutinating cancer cells. Namely, lectin binds to a carbohydrate with a specific structure and thus enables the selective communication between the cells with the lectin substance and the cells with a carbohydrate which binds to it.

The studies on lectin are considered as an important field in elucidating the mechanism of intracellular communications by molecular recognition, and, at present, with centering around the elucidation of the recognition mechanism at the molecular and cellular levels, the studies in aspect of nervous system, immune system, inflammation response, etc. and those in aspect of the relation between infection, diseases(cancer, rheumatism) and carbohydrates are extensively carried out.

Especially, it has been proven that carbohydrate chain of the cell membrane surface in connection with cancers is an important factor which decides the metastasis of cancer in the experimental model, and this fact is supported from the research reports that the surface carbohydrate chains of the cancer variants which differ in the metastasis are different in the lectin binding specificity, metastasis of cancer cells selected in vitro using lectins is different from each other, and it is possible to change the metastasis by modifying the carbohydrate chains of cancer cells. These characteristics are known to be common regardless of the kind of cancer cells, and the organ which is the target of metastasis. The metastatic tumor, is one of the greatest causes which make the treatment of malignant tumors difficult since it frequently appears with the lapse of time even after the complete removal of the primary tumors with surgical treatment such as operation. From these view points, the studies on the cases of using asialoglycoprotein as a carrier, and using polymers modifying carbohydrate chains, targeting of the protein pharmaceuticals by the carbohydrate modification and carbohydrate chain introduction by the micro-particulate carrier have recently been carried out in conjugation with cancers. Especially, the carbohydrate recognition mechanism which is often used in the targeting of systemic drugs includes, for example, a galactose receptor existing on the liver parenchymal cell surface, a mannose receptor on the various macrophages including kupffer cell, etc. These receptors have high affinity and are specifically expressed on the respective organs and cells, and cellular specific targeting of drugs using these mechanisms thus is expected.

Since the latest reports on the structural change of carbohydrate of proteins within the living body upon invasion of rheumatism, cancer or AIDS, there have been attempts to explain the results of these diseases in view of the structural changes of carbohydrate. Especially, it is considered that the remarkable change of sialyl epitopes in the sialoglycoconjugate of the surface of pathogenic or tumor cells results from the kind of sialic acid in the oligosaccharides or the carbohydrate binding pattern with the adjacent carbohydrates. Therefore, lectins specifically recognizing various sialic acids and their carbohydrate binding patterns can be used as a tool for identifying various sialyl epitopes in the biopsy of pathogens or malignant tumors.

Sialic acid refers to about 30 compounds including N-acetylneuraminic acid or its derivatives such as N-glycolylneuraminic acid, an acyl substituent at the C-5 amino group. Most of the other sialic acids have O-acetyl substituent(s) of one or more C-4, C-7, C-8 or C-9 hydroxyl groups. The thus substituted sialic acids may cause transformation or other changes in the cellular environment and has known to inhibit or weaken the sialic acid hydrolase of bacteria or viruses to change their immunity, thus affecting the enzyme activity in the catabolism of complex carbohydrates.

Most of the lectins are reported to specifically recognize D-mannose and D-galactose, and those which can specifically recognize N-acetylneuraminic acids that play important structural and functional roles at the non-reduced terminal of oligosaccharide are few. N-acetylneuraminic acid-binding lectins are mainly found in Wheat germ agglutinin (WGA), *Maackia amurensis* agglutinin), *Limulus polyphemus* lectin (limulin), *Sambucus niger* agglutinin (SNA). Among them, there are many reports that the plant originated lectins exert anti-cancer effect that inhibits cancer growth and anti-tumor effect that inhibits cancer development due to carcinogens. WGA and MAA have been known to have a cytotoxic effect against hepatoma, melanoma, choriocarcinoma, osteosarcoma, etc. and have inhibiting effects against murine ascitic tumor and murine ascitic lymphoma tumor in vivo, and human nasal septum tumor, human colon adenocarcinoma, murine embryonal carcinoma in vitro. MAA and SNA were reported to be selective against the receptor of Influenza A virus. In addition, WGA is used in the carbohydrate structure analysis of HIV and SNA is used in identifying N-acetylneuraminic acid in hepatoma cells (Abdullaev F. et al. Natural Toxin 5, 157–163, 1997).

In addition, it has been reported that the increase or dramatic change in the carbohydrate chains containing N-acetylneuraminic acid and the corresponding increase of the lectin-binding are closely related each other in many cancer-related experimental models. Such an increase in N-acetylneuraminic acid also appeared in the N- or O-bound oligosaccharides of glycoprotein concurrently. The inhibition of carbohydrate chain formation by the carbohydrate chain formation inhibitor such as tunicamycin results in the decrease of metastasis and, in connection with the glycolipids, there are increases in the gangliosides and in the carbohydrate chains containing neuraminic acid. Recently, IGR39 of the primary tumor among the human melanoma cell lines isolated from the patients with the same cancer and IGR37 originated from metastatic lymph node are reported to strongly bind to lectins. An affinity column in which lectin is bound to sepharose is used in isolating and purifying mucin-type glycoprotein from the plasma membrane of HM7 melanoma cell line. Also, a material in which lectin is bound to fluorochrome tetramethylodamine isothiocynate is used for effective detection in the B16F10 melanoma and Lewis lung carcinoma cells. Meantime, the possibility of letctin as a carrier protein was reported by making an acid-labile chemotherapeutic prodrug in which lectin is bound to doxorubicin against colon carcinoma.

The present invention has been accomplished by conducting various experiments with the Korean legume *Maackia fauriei* in order to find out a useful material from the living things in nature.

Therefore, the present invention in one aspect provides a lectin MFA which is a kind of proteins specifically recognizing to N-acetylneuraminic acid, the MFA being isolated from the Korean legume *Maackia fauriei*.

The above lectin component has a molecular weight of approximately 30.0 kDa by the electrophoresis and the mass spectrometry and about 104,580 Da by the gel filtration chromatography and its N-terminal amino acid sequence is represented in sequence no. 1 of the sequence listing. This lectin component was proven to bind N-acetylneuraminic acid or a glycoprotein containing N-acetylneuraminic acid by hemagglutination reaction and hemagglutination-inhibition reaction.

The present invention in another aspect provides a process for preparing the lectin MFA from the Korean legume *Maackia fauriei*.

Specifically, the lectin MFA can be prepared by removing the outer coat from the bark of *Maackia fauriei*, homogenizing the bark and mixing the homogenate with an aqueous 0.15M NaCl solution under stirring for 24 hrs at 4° C., filtering the precipitate with a filter, applying the filtrate onto Sepharose CL-6B column chromatography to give the crude fractions and further purifying the active fraction through a fetuin-affinity column to give the above protein component.

The present invention in further aspect provides the use of the lectin MFA as diagnostics for a disease in which the structure of carbohydrates within the cells contains N-acetylneuraminic acid and its distribution is changed due to invasion of diseases, which comprises the lectin MFA. The examples of the disease may include, but not limited thereto, hepatoma, melanoma, choriocarcinoma, osteosarcoma, and colon cancer, etc.

As result of testing biological activity, the lectin MFA was shown to specifically binds to N-acetylneuraminic acid as a monosaccharide and to fetuin containing N-acetylneuraminic acid as a glycoprotein. Therefore, the lectin MFA can be used as diagnostics for the diseases of hepatoma, melanoma, choriocarcinoma, osteosarcoma, and colon cancer, etc based on this activity.

The present invention in still further aspect provides a use of the lectin MFA as an anti-proliferation agent against cancer cells.

The lectin MFA according to the present invention can be used as diagnostics or a carrier protein since it selectively recognizes and binds to N-acetylneuraminic acid or a glycoprotein containing N-acetylneuraminic acid as demonstrated by the hemagglutination reaction, hemagglutination-inhibition reaction. In addition, the lectin MFA itself has an anti-cancer effect as shown in the test examples which will be described in detail. Therefore, the lectin MFA of the invention can also be used as an active component of an anti-proliferation agent against cancer cells (or an anti-cancer agent) in diseases in which N-acetylneuraminic acid exists. Examples of the diseases may include, but not limited thereto, breast cancer, melanoma, or hepatoma.

The pharmaceutical composition of the anti-proliferation agent against cancer cells according to the present invention can be prepared in combination with the conventional pharmaceutically acceptable carrier. Generally, the active component is mixed with a pharmaceutically acceptable liquid or solid carrier. If necessary, additives such as solvent, dispersant, emulsifier, buffer, stabilizer, diluent, binder, disintegrant, lubricant, etc. can be used. The composition may be in the form of solid formulations such as tablet, granule, powder or capsule, or liquid formulations such as normal liquid, suspension or oil. These formulations may also be made as dry preparations which can be used in the liquid form by addition of a proper carrier before use.

The pharmaceutical composition of the present invention can be administered orally or parenterally, i.e., by way of injection or drop means.

The pharmaceutically acceptable carriers may be selected according to the mode of administration and formulation. In case of oral formulations, for example, the carriers include starch, lactose, refined sugar, mannite, carboxymethylcellulose, corn starch, or inorganic salts. In the preparation of oral formulations, binder, disintegrant, surfactant, lubricant, fluidity enhancer, sweetening agent, coloring agent or spicery can be additionally used.

The parenteral formulation is prepared by dissolving or suspending the composition containing the lectin MFA as the active component of the present invention in a diluent, such as distilled water for injection, physiological salt solution, aqueous glucose solution, vegetable oil for injection, sesame oil, peanut oil, soybean oil, corn oil, propylene glycol or polyethylene glycol and, if necessary, adding disinfectant, stabilizer, tonic agent or analgesic agent. The pharmaceutical composition of the invention can be administered via a proper route depending on the formulation. The administration mode includes, but not specifically limited to, internal, external or injection. For injection administration, intravenous, intrmuscular; subcutaneous or intradermal injection is possible.

The amount of the pharmaceutical composition to be administered can properly be determined according to the formulation, the administration route, the purpose of use and the patient's age, weight or symptoms. The amount of the active component in the preparation is, for example, 10 μg to 200 mg/kg (weight) a day for an adult. Of course, the dosage varies depending on the conditions and the actual dosage may be greater or less than the above range.

The present invention in still further aspect provides a drug conjugate in which the lectin MFA as a carrier protein for local transport of a drug and a selective drug for a disease as an active agent (for example, an anti-cancer drug) are bonded. Examples of the diseases may include, but not limited thereto, hepatoma, melanoma, choriocarcinoma, osteosarcoma, and colon cancer, etc.

The present invention in still further aspect provides uses of the lectin MFA in the research material of immunobiochemistry or in agglutination of cancer cells.

Since the lectin MFA of the invention selectively recognizes and binds to N-acetylneuraminic acid or a glycoprotein containing N-acetylneuraminic acid as demonstrated by the hemagglutination reaction, hemagglutination-inhibition reaction, the lectin MFA according to the present invention can be used as the research materials of immuno-biochemistry or in agglutination of cancer cells based on this principle.

Hereinafter, the present invention will be described in detail by way of the following examples, which are not intended to limit the scope of the present invention.

EXAMPLE 1

Isolation of Protein Eluate Containing the Lectin MFA from Korean Legume *Maackia fauriei*

The collected Korean legume *Maackia fauriei* was washed with distilled water and the outer coats of the trunks were removed. Then, the bark was homogenized and mixed with an aqueous 0.15M NaCl solution under stirring for 24 hrs at 4° C. The homogenate was first filtered with a 0.6 μm membrane filter and then with a 0.45 μm membrane filter. The filtrate was concentrated into about 10 folds using a protein concentrator (Model: Stirred Cell, Manufacturer: Amicon). The concentrated crude protein extract was applied directly onto a Sepharose CL-6B column (Model: Econo Pac Column, Manufacturer: Bio-Rad), which had been filled with 10 ml of gel and equilibrated with 10 mM Tris-HCl (pH 7.5) containing 0.15 M NaCl. To the column, 1 ml of the 10×fold concentrate of the plant *Maackia fauriei* bark was run to give a total of 50 fractions. The resulting chromatogram was made by recording absorbance at 280 nm with a UV/VIS spectrometer. The results were represented in FIG. 1. From the chromatogram by the Sepharose CL-6B, the fractions from 9 to 17 with hemagglutination activity were collected to isolate protein eluate containing MFA.

EXAMPLE 2

Isolation of the Lectin MFA from the Protein Eluate of *Maackia fauriei*

Figure 2:
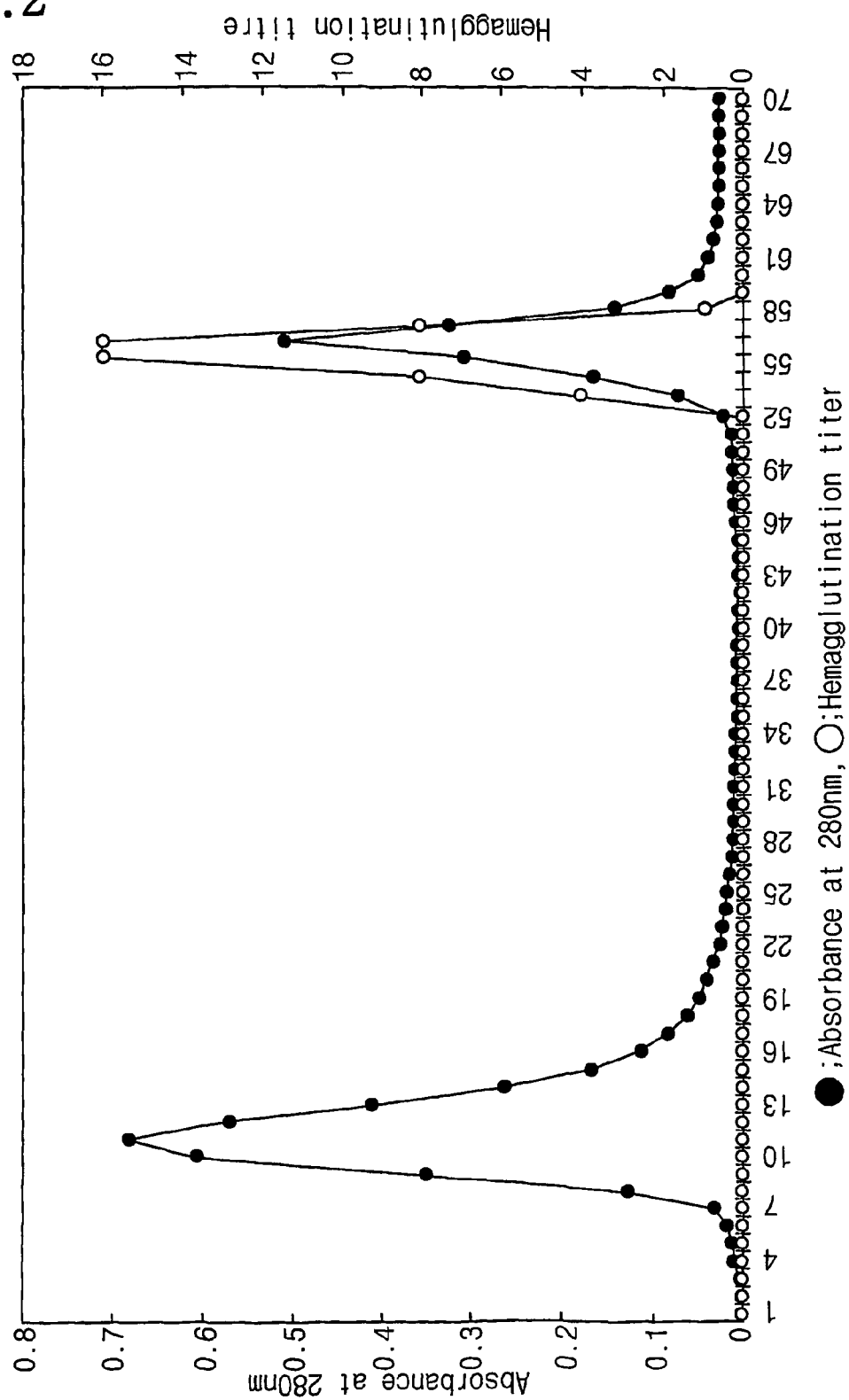
FIG. 2 is a graph showing a UV (280 nm) spectroscopic chromatogram and hemagglutination response by a fetuin-affinity column of the lectin MFA prepared by the present invention.

Among the protein solutions obtained from the Example 1, 1 ml was applied onto a fetuin-affinity column to obtain a total of 70 fractions. The resulting chromatogram was made by recording absorbance at 280 nm with a UV/VIS spectrometer. The results were represented in FIG. 2. After loading the fractions onto the fetuin-affinity column, the column was allowed to stand for 1 hr at room temperature and 10 mM Tris-HCl (pH 7.5) containing 0.15 M NaCl were slowly run and each 1 ml of fraction was collected. Subsequently, 10 mM Tris-HCl (pH 7.5) containing 0.15 M NaCl were run until the absorbance value at 280 nm reaches 0.0. Then, the faction nos. 8 to 16 with the absorbance of 0.1 or more were collected, and the fractions were confirmed as not containing lectin component by the hemagglutination response which will be described in detail. The fractions after fraction no. 36 representing the absorbance value of completely 0.0 were rapidly run on 50 mM glycine buffer (pH 3.0) to collect 1 ml of fractions. The eluted fractions were immediately neutralized with 1.5 M Tris-HCl (pH 8.5). However, it was confirmed that these fractions do not reveal the bound lectin as a result of determining the absorbance at 280 nm. Subsequently, the fraction from fraction no. 46 were rapidly run on the fetuin-affinity column eluting with 0.1 N NaOH to collect 1 ml of fractions. The eluted fractions were immediately neutralized with 1.5 N HCl. As a result of determining the absorbance at 280 for the fractions, it was confirmed that the fraction nos. 53 to 58 showed a high absorbance. In addition, after conducting the hemagglutination response for these fractions, it was confirmed that they were lectin with high activity.

The amount of the total protein, activity and the recovery of the lectin MFA obtained from the Examples 1 and 2 are as shown in the following Table 1.

TABLE 1

| Purification step | Protein (mg/ml) | Specific activity(unit/1 mg/ml) | MFA Recovery (%) |
|---|---|---|---|
| Crude extract | 525.0 | 731 | 100.0 |
| Concentrated crude extract | 245.0 | 1170 | 46.7 |
| Sepharose CL-6B column, fraction nos. 9 to 17(protein solution) | 147.0 | 1706 | 28.0 |
| Fetuin-affinity column, fraction nos. 53 to 58(MFA) | 25.5 | 1969 | 4.9 |

The specific activity of the table 1 represents the unit of lectin contained in 1 mg/ml of protein and the unit represents the dilution fold which revealed hemagglutination response. It was confirmed that the final recovery yield of MFA from the crude extract of *Maackia fauriei* was no less than 4.9%.

EXAMPLE 3

Determination of Purity and Molecular Weight of the Lectin MFA

To determine the molecular weight and the purity of the nos. 9 to 17 fractions by Sepharose CL-6B, that is the fraction (A) before applying on the fetuin-affinity colum in the Example 1, the lectin component-containing fraction nos. 53 to 58 which were obtained from the fetuin-affinity chromatography (B) (this was identified as lectin MFA by the same methods as Examples 4 and 5) and the unbound fraction nos. 8 to 16 (C) by the fetuin-affinity column, an electrophoresis analysis, a gel filtration chromatography and a MALDI-TOF mass spectrometry analysis were performed.

First, electrophoresis was performed for the above fractions A, B and C on a 12% polyacrylamide gel including 0.1% SDS to compare the molecular weight with the standard molecular marker. After the running, the protein band was stained with a coomassie blue reagent. The results are shown in FIG. 3, in which lane 1 is a moleculelar marker (kDa); lane 2 is Sepharose CL-6B fractions of *Maackia fauriei* (corresponding to the above fraction A); lane 3 is the isolated lectin MFA of *Maackia fauriei* (corresponding to the above fraction B); and lane 4 is the unbound fraction from the fetuin-affinity column(corresponding to the above fraction C).

Figure 3:
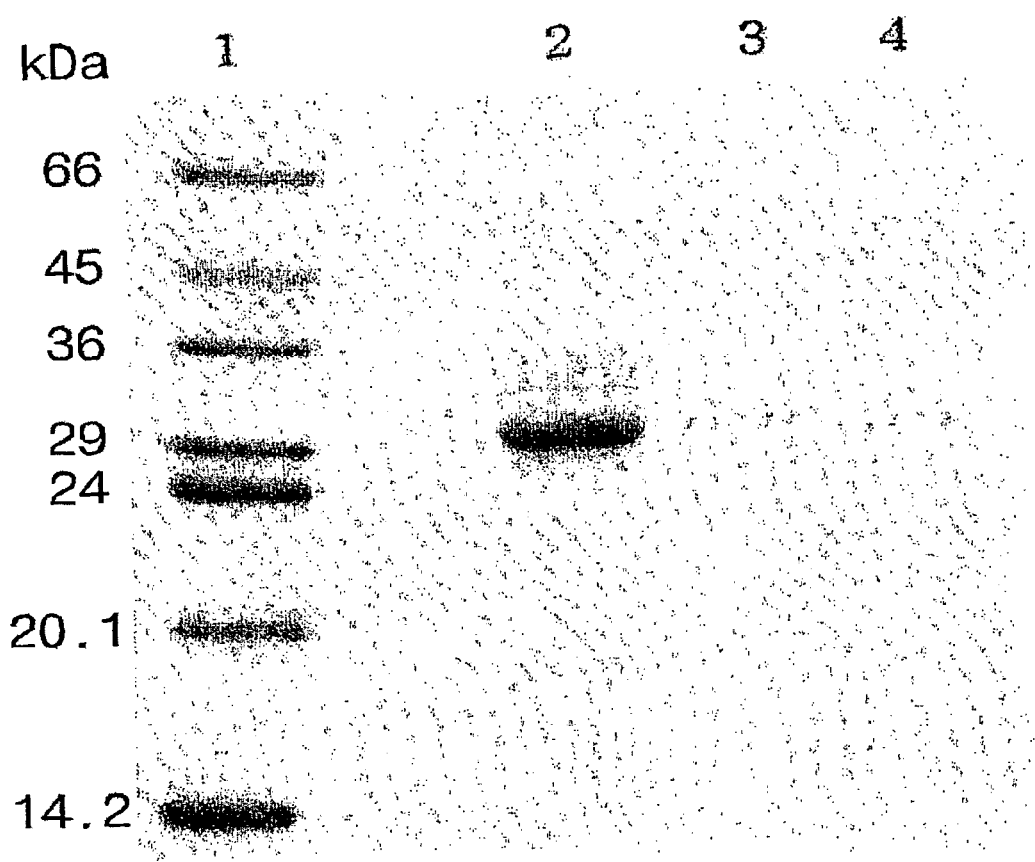
FIG. 3 is a photograph showing an electrophoretic analysis of the lectin MFA prepared by the present invention, in which lane 1 is a molecular weight marker (66, 45, 36, 29, 24, 20.1, 14.2 kDa); lane 2 is a Sepharose CL-6B eluate of *Maackia fauriei* (fraction nos. 9 to 17); lane 3 is the lectin MFA of *Maackia faurie* by a fetuin-affinity column(fraction nos. 53 to 58) and lane 4 is unbound eluate by the fetuin-affinity column(fraction nos. 8 to 16)

As can be confirmed from the results of the electrophoresis in FIG. 3, one band having a molecular weight of approximately 30.0 kDa was detected stating that a pure state of lectin was isolated.

Figure 4:
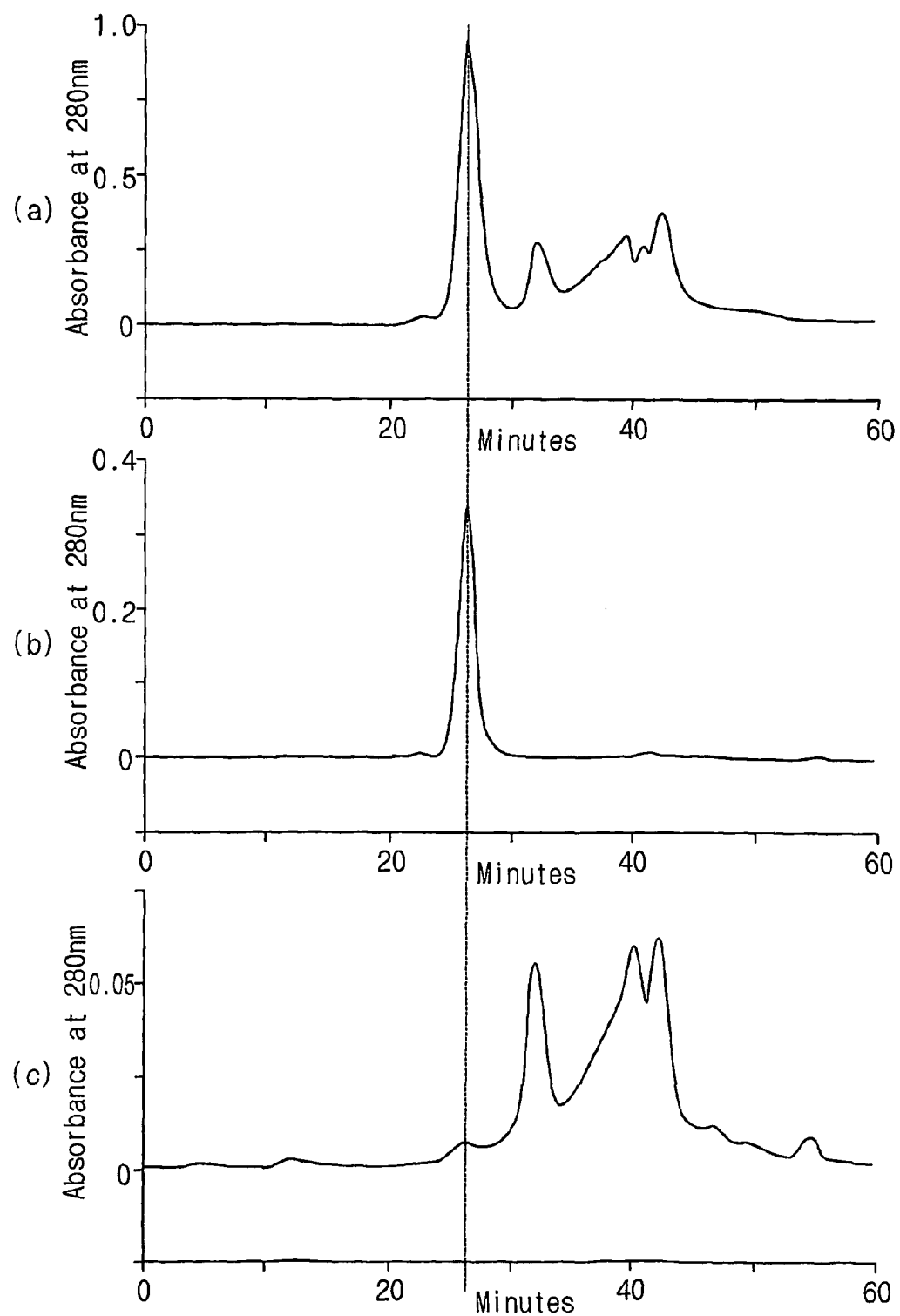
FIG. 4 is a graph showing the results of a UV (280 nm) spectroscopic chromatogram by a gel filtration of MFA prepared by the process of the invention, in which graph (a) represents an eluate of the lectin MFA of *Maackia faurie* on a Superdex-200 HR column(fraction nos. 9 to 17), (b) represents an eluted lectin MFA of *Maackia faurie* on a fetuin-affinity column(fraction nos. 53 to 58) and graph (c) represents unbound eluate by the fetuin-affinity column (fraction nos. 8 to 16)

In the meantime, the gel filtration chromatography was performed using Superdex-200 HR column (Pharmacia) equilibrated with 10 MM phosphate buffer, 150 mM NaCl (pH 7.2) at a flow rate of 0.5 ml/min. The results are shown in FIG. 4, in which lane (a) is Sepharose CL-6B fractions of *Maackia fauriei* (corresponding to the above fraction A); lane (b) is the isolated lectin MFA of *Maackia fauriei* (corresponding to the above fraction B); and lane (c) is the unbound fraction from the fetuin-affinity column(corresponding to the above fraction C). The lectin component B by the gel-filtration chromatography also revealed a single peak and impurity C which had not been bound to the fetuin affinity column was completely removed from the fraction A before the fetuin-affinity column isolation.

Figure 5:
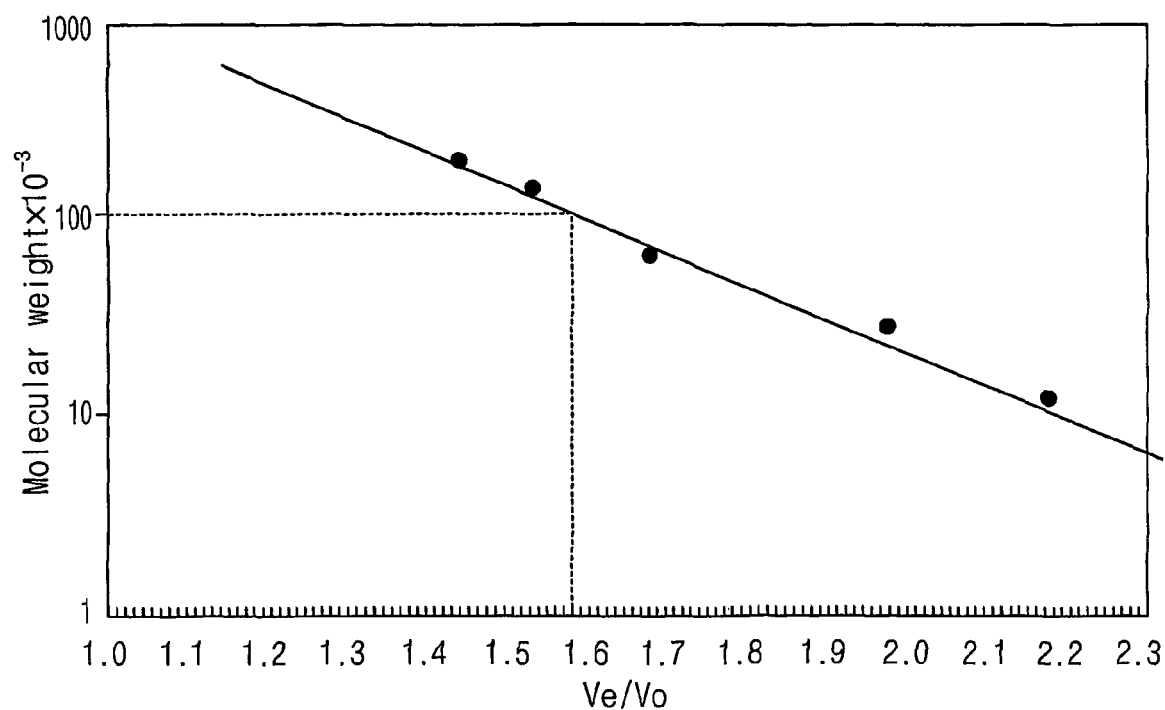
FIG. 5 is a graph showing the molecular weight by the gel filtration column of the lectin MFA prepared by the process of the invention. Molecular weight marker(200, 150, 66, 29, 12.4 kDa)

In addition, the molecular weight of MFA fractions obtained by the gel filtration chromatography was compared with the molecular weight standards (200, 150, 66, 29, 12.4 kDa) and conformed the molecular weight from Ve/Vo (elution volume/elution volume for blue dextran) to determined as 104,580 Da. The results are shown in FIG. 5.

Figure 6:
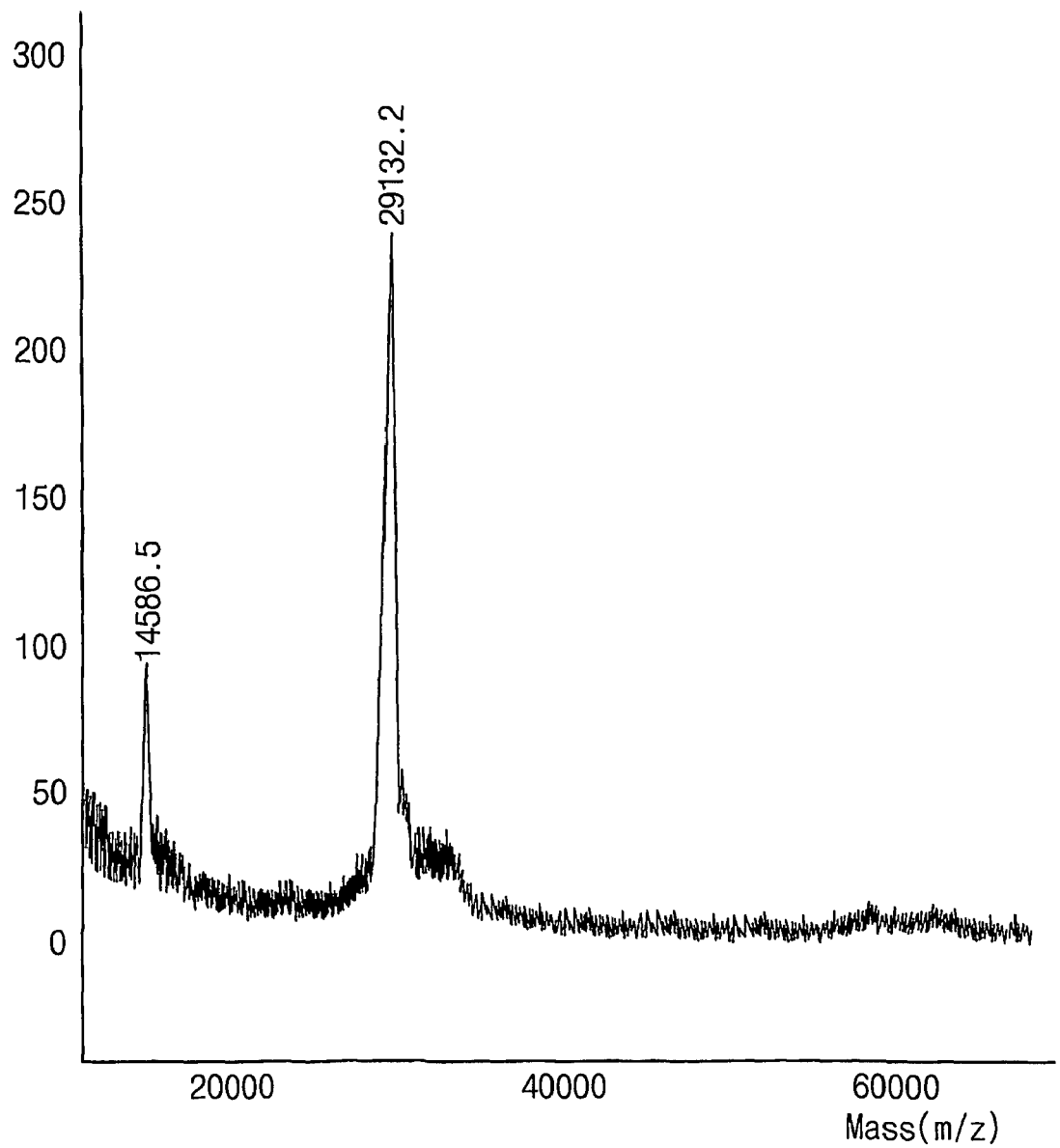
FIG. 6 is a graph showing the molecular weight by MALDI-TOF mass spectrometer of the lectin MFA prepared by the process of the invention.

The molecular weight was further determined by matrix-assisted laser desorption/ionization time-of-flight mass spectrometry (Model: Voyager™ RP, Manufacturer: Perseptive Biosystems) to be m/z 29132.2 and the result is shown in FIG. 6.

The molecular weight of the lectin MFA by the above electrophoresis, gel-filtration chromatography, and mass spectrometry was exhibited to be approximately 30.0 kDa by the electrophoresis, 29,132.2 Da by the mass spectrometry and 104,580 Da by the gel-filtration chromatography.

EXAMPLE 4

Analysis of N-Terminal Amino Acid of the Lectin MFA

The N-terminal amino acid of the lectin MFA isolated from *Maackia fauriei* was determined with an amino acid sequencer (Model: Automatic Protein Sequencer, 476A-01-120, Manufacturer: Applied biosystems) according to the manufacturer's instructions. It was revealed that the N-terminal amino acid sequence contains Ser-Asp-Glu-Leu-Ser-Phe-Asn-Ile-Asn-Asn-Phe-Val-Pro-Asn-Gln-Ala-Asp-Leu-Leu-Phe (Sequence No. 1).

EXAMPLE 5

Hemagglutination Assay of the Lectin MFA

Hemagglutination assay was performed using the nos. 53–58 fractions in the chromatogram obtained in Example 2 by diluting human, mouse, rat and rabbit sera with a 10 mM phosphate buffer and 0.15M NaCl (pH 7.2) to a concentration of 6.25%. The fractions revealed positive response in the assay were collected and subjected to electrophoresis and gel-filtration chromatography as shown in the example 3 to detect a single band, which was designated as MFA (*Maackia fauriei* agglutinin). Human blood group (A, B and O type), dog, mouse, rat and rabbit erythrocytes were diluted in the same manner as described above. Each 100 µl of the erythrocytes was allowed to stand at room temperature together with 100 µl of the lectin MFA to detect the hemagglutination reaction. As a result, an agglutination was observed in the human erythrocyte that includes only N-acetylneuraminic acid. However, agglutination occurred in the mouse and rat erythrocytes (diluted up to 1024-fold) and the rabbit erythrocyte (diluted up to 128-fold) that include N-glycolylneuraminic acid. The results are as shown in Table 2.

TABLE 2

| Erythrocyte | Type of sialic acid | Minimal hemagglutination inhibiting activity |
|---|---|---|
| Human type A | NeuAc | 256 |
| Human type B | NeuAc | 256 |
| Human type O | NeuAc | 256 |
| Mouse | NeuGc, NeuAc, O-acetylsialic acid | 1024 |

TABLE 2-continued

| Erythrocyte | Type of sialic acid | Minimal hemagglutination inhibiting activity |
|---|---|---|
| Rat | NeuGc, NeuAc, O-acetylsialic acid | 1024 |
| Rabbit | NeuGc, NeuAc, O-acetylsialic acid | 128 |

Note:
The number of minimal hemagglutination inhibiting activity represents the minimal dilution folds obtained by diluting the lectin MFA two-fold against each erythrocyte diluted to 6.25%, where NeuGc is N-glycolyl-neuraminic acid, and NeuAc is N-acetylneuraminic acid.

The above results show that the lectin MFA selectively recognizes N-acetylneuraminic acid only and inhibits agglutination of the lectin MFA up to 256-fold dilution in the human erythrocyte, this indicating that the lectin MFA exists at a concentration of about 256 µg/ml since the above value is the minimum concentration for agglutination in the case where the concentration of the concentrated lectin solution is about 1 µg/ml.

EXAMPLE 5

Hemagglutination-Inhibition Assay of the Lectin MFA

In order to confirm that the lectin MFA of the present invention recognizes N-acetylneuraminic acid, hemagglutination-inhibition reaction was performed using monosaccharide, disaccharide and glycoprotein. 50 µl of a 128-fold diluted solution of lectin MFA in 0.15 M NaCl and 50 µl of each 1 mg/ml solution of monosaccharides (e.g., β-D-glucose, D-galactose, L-fucose, D-mannose, N-acetylneuraminic acid, N-glycolylneuraminic acid, N-acetyl-D-glucosamine, N-acetyl-D-galactosamine and methyl-α-D-glucopyranoside), disaccharide (e.g., α-lactose, β-lactose, D-lactose, β-gentiobiose, maltose, D-raffinose or D-cellobiose) and glycoprotein (e.g., fetuin and asialofetuin) in 0.15 M NaCl were added to the each well of a 96-well microplate. After the reaction for one hour or more at room temperature, 50 µl of the erythrocyte suspended in 0.15 M NaCl was added to each well and reacted for one hour at room temperature. As a result, N-acetylneuraminic acid as a monosaccharide, and fetuin containing N-acetylneuraminic acid as glycoproteins only inhibited the agglutination, while the other monosaccharides, disaccharides and glucoproteins did not inhibit agglutination. The results are as shown in Table 3.

TABLE 3

| Division | Carbohydrate | Type of sialic acid | Minimum erythrocyte agglutination inhibition concentration |
|---|---|---|---|
| Monosaccharide | β-D-glucose | — | — |
| | D-galactose | — | — |
| | L-fucose | — | — |
| | D-mannose | — | — |
| | N-acetylneuraminic acid | NeuAc | 10.0 mM |
| | N-glycolylneuraminic acid | — | — |
| | N-acetyl-D-glucosamine | — | — |
| | N-acetyl-D-galactosamine | — | — |
| | Methyl-α-D-glucopyranoside | — | — |

TABLE 3-continued

| Division | Carbohydrate | Type of sialic acid | Minimum erythrocyte agglutination inhibition concentration |
|---|---|---|---|
| Disaccharide | α-lactose | — | — |
| | β-lactose | — | — |
| | D-lactose | — | — |
| | β-gentiobiose | — | — |
| | Maltose | — | — |
| | D-raffinose | — | — |
| | D-cellobiose | — | — |
| Glycoprotein | Fetuin | NeuAc | 5.2 μM |
| | Asialofetuin | — | — |

In Table 3, the minimum hemagglutination-inhibition concentration represents the minimum concentration for the 6.25% mouse erythrocyte which revealed the minimum hemagglutination-inhibition by diluting the lectin MFA to 128-folds that showed minimum agglutination and diluting 2-folds each concentration of monosaccharide, disaccharide and glycoprotein. The negative sign (−) means that there is no hemagglutination-inhibition. Monosaccharides and disaccharides(except for N-acetylactosamine) did not show hemagglutination inhibition at 100 μM and N-acetylactosamine did not show hemagglutination inhibition at 10 mM. NeuGc and NeuAc represent N-glycolylneuraminic acid and N-acetylneuraminic acid, respectively.

EXAMPLE 7

Amino Acid Composition Analysis of the Lectin MFA

Amino acid composition of the lectin MFA was analysed with an amino acid analyzer (Model: Biochrom 20 Auto-Amino Acid Analyzer, Manufacturer: Pharmacia) according to the manufactur's instructions. The results are set forth in Table 4 below.

TABLE 4

| Amino acid | Mol(%) |
|---|---|
| Asx | 12.2 |
| Glx | 5.6 |
| Ser | 10.5 |
| Thr | 8.5 |
| Pro | 5.9 |
| Gly | 5.7 |
| Ala | 8.2 |
| Cys | 0.8 |
| Val | 9.8 |
| Met | 0.0 |
| Ile | 6.1 |
| Leu | 8.1 |
| Tyr | 3.4 |
| Phe | 7.8 |
| His | 1.6 |
| Lys | 3.1 |
| Arg | 2.6 |

Asx represents asparaginic acid and asparagine, and Glx represents glutamic acid and glutamine.

EXAMPLE 8

Comparion of Binding Specificity of N-acetylneuraminic acid-Binding Letcin

The binding specificity of the MFA with Wheat germ agglutinin, *Maackia amurensis* aggulutinin, *Limulus polyphemus* lectin, and *Sambucus niger* agglutinin which have already been reported to recognize N-acetylneuraminic acid was determined by a hemagglutination inhibition response using 10 mM of N-acetylneuraminic acid and N-acetylneuraminic acid-binding fetuin. As a result, only MFA revealed hemagglutination inhibition at 10 mM N-acetylneuraminic acid, and in the case of fetuin, MFA revealed the lowest hemagglutination inhibition. The results are set forth in Table 5 below.

TABLE 5

| | Minimum hemagglutination-inhibition concentration | |
|---|---|---|
| Lectin | N-acetylneuraminic acid | Fetuin |
| Wheat germ agglutinin | — | 207 μM |
| Maackiaa murensis agglutinin | — | 10.4 μM |
| Limulus polyphemus lectin | — | 10.4 μM |
| Sambucus niger agglutinin | — | 12.9 μM |
| MFA | 10.0 mM | 5.2 μM |

In Table 5, the minimum hemagglutination-inhibition concentration represents the minimum concentration for the 6.25% human B type erythrocyte which revealed the minimum hemagglutination-inhibition. The negative sign (−) means no hemagglutination inhibition up to 10 mM

EXAMPLE 9

Effect of Metal Cations on the MFA

It has generally known that lectin lost activity if $Ca^{2+}$ or $Mn^{2+}$ is removed. In order to confirm this, the *Maackia fauriei* lectin MFA was dialyzed overnight against 0.1 M ethylenediaminetetraacetic acid (EDTA) disodium salt and then against 10 mM Tris-HCl (pH 7.5) containing 0.15 M NaCl three times, after which it was added 0–50 mM $CaCl_2$ and $MnCl_2$ to analyze the effect. As can be seen from the result in Table 6, the *Maackia fauriei* lectin MFA in which $Ca^{2+}$ or $Mn^{2+}$ was removed by EDTA lost activity, but activity was fully restored with the addition of 25 mM $CaCl_2$, 25 mM $MnCl_2$, and 25 mM $CaCl_2$ and 25 mM $MnCl_2$.

TABLE 6

| Cations | Concentration | Activity |
|---|---|---|
| $CaCl_2$ | 3.125 mM | 40% |
| | 6.25 mM | 60% |
| | 12.5 mM | 80% |
| | 25 mM | 100% |
| | 50 mM | 100% |
| $MnCl_2$ | 3.125 mM | 60% |
| | 6.25 mM | 80% |
| | 12.5 mM | 90% |
| | 25 mM | 100% |
| | 50 mM | 100% |
| $CaCl_2 + MnCl_2$ | 3.125 mM | 70% |
| | 6.25 mM | 70% |
| | 12.5 mM | 90% |
| | 25 mM | 100% |
| | 50 mM | 100% |

EXAMPLE 10

Effect of temperature on the MFA

In order to confirm the effect of temperature, the *Maackia fauriei* lectin MFA was allowed to stand for 1 hr at 4° C., 15° C., 25° C., 37° C., 45° C., 50° C., 55° C. and 60° C. As a result of measurement of the activity in Table 7 below, the lectin MFA showed 100% activity at the temperature range below 50° C.

TABLE 7

| Temperature | Activity |
| --- | --- |
| 4° C. | 100% |
| 15° C. | 100% |
| 25° C. | 100% |
| 37° C. | 100% |
| 45° C. | 100% |
| 50° C. | 100% |
| 55° C. | 50% |
| 60° C. | 50% |

EXAMPLE 11

Effect of pH on the MFA

The effect of pH on the *Maackia fauriei* lectin MFA was determined at 25 mM KCl-HCl (pH 1.96, 3.16), 20 mM glycine-HCl (pH 4.04, 5.63, 6.00), 20 mM Tris-HCl (pH 7.34, 9.06), and 25 mM sodium carbonate-HCl (pH 10.08, 10.89). The results are shown in Table 8 below. As can be seen from the table, MFA revealed its 100% activity at pH 4.04~pH 7.34.

TABLE 8

| Buffer (pH) | Activity |
| --- | --- |
| 25 mM KCl-HCl (pH 1.96) | 10% |
| 25 mM KCl-HCl (pH 3.16) | 10% |
| 20 mM glycine-HCl (pH 4.04) | 100% |
| 20 mM glycine-HCl (pH 5.63) | 100% |
| 20 mM glycine-HCl (pH 6.00) | 100% |
| 20 mM Tris-HCl (pH 7.34) | 100% |
| 20 mM Tris-HCl (pH 9.06) | 50% |
| 25 mM sodium carbonate-HCl (pH 10.08) | 50% |
| 25 mM sodium carbonate-HCl (pH 10.89) | 10% |

EXAMPLE 12

Anti-Proliferation Effect of the Lectin MFA on Cancer Cell

The anti-proliferation effect of the lectin MFA on cancer cells was evaluated using MTT(3-[4,5-dimethyldiazol-2-yl]-2,5-diphenyl tetrazolium bromide) assay (See Mosmann T et al., J. Immunol. Methods 65, pp 55–63 (1983)). Each cancer cell was cultured in a 90% RPMI 1640-10% FBS (fatal bovine serum) medium. Using a hematocytometer, the number of cells was determined as about $1 \times 10^4$ per 100 µl. Then, the sample was added to the wells of a 96-well microplate. After addition of each 100 µl of 8, 0.8 and 0.08 µM lectin MFA, the plate was allowed to stand for 72 hours in an incubator maintaining 5% $CO_2$. To each well were added 50 µl of the MTT reagent and allowed to stand for 4 hours at the $CO_2$ incubator. After discarding the supernatant and adding 150 µl of dimethyl sulfoxide, the sample solution was mixed for 10 minutes and measured the absorbance at 540 nm with the microplate. As a control, the same experimental procedure was performed under the above conditions without adding the lectin MFA.

The percentage of proliferation was designated as 100% for the control and the relatively decreased percentage of proliferation for the samples containing the lectin MFA was compared to the control. The same procedures were repeated three times to express the decreased percentage as average value ± standard deviation. As can be seen from the results of Table 9, lectin MFA exerted anti-proliferation effects on cancer cells, breast cancer MCF-7, melanoma G-361 and hepatoma SNU-449 cells in a dose dependent manner.

TABLE 9

| Origin of cancer cell | Name of Cancer | Composition of medium | Concentration of lectin MFA | Anti-proliferation % |
| --- | --- | --- | --- | --- |
| Breast cancer | MCF-7 | RPMI 1640 90%, FBS 10% | 8 µM | 54.1 ± 3.9% |
| | | | 0.8 µM | 36.4 ± 5.9% |
| | | | 0.08 µM | 12.6 ± 2.9% |
| Melanoma | G-361 | RPMI 1640 90%, FBS 10% | 8 µM | 33.2 ± 8.7% |
| | | | 0.8 µM | 23.6 ± 2.6% |
| | | | 0.08 µM | 3.3 ± 1.3% |
| Hepatoma | SNU-449 | RPMI 1640 90%, FBS 10% | 8 µM | 35.6 ± 1.7% |
| | | | 0.8 µM | 17.5 ± 1.0% |
| | | | 0.08 µM | 7.2 ± 0.7% |

EXAMPLE 13

Pharmaceutical Preparation

Type of Preparation (tablet)

| | |
| --- | --- |
| Active component (lectin MFA) | 10 mg |
| Lactose | 80 mg |
| Starch | 17 mg |
| Magnesium stearate | 3 mg |
| Crystalline cellulose | 10 mg |

The tablets were prepared by the conventional method so as to contain the above-mentioned ingredients per tablet. If necessary, the tablets may additionally include an enteric coating (e.g., hydroxypropylmethylcellulose phthalate), a sugar coating or a film (e.g., ethyl cellulose).

INDUSTRIAL APPLICABILITY

The lectin MFA in accordance with the present invention can be used as reagents for carbohydrate-related researches based on the principle that it specifically recognizes N-acetylneuraminic acid as well as diagnostics for a disease in which the distribution of N-acetylneuraminic acid is changed due to invasion of diseases. It can also be used as a carrier protein for local transport of a selective drug, in which side effect is minimized by conjugating lectin with anti-cancer agents, and an anti-proliferation agent for cancer cells of breast cancer, melanoma, and hepatoma.

What is claimed is:

1. A lectin MFA (*Maackia fauriei* agglutinin) protein extracted from the Korean legume *Maackia fauriei* characterized in that it has a molecular weight of approximately 30.0 kDa by electrophoresis and mass spectrometry and its N-terminal amino acid sequence is represented in SEQ ID NO: 1 of the sequence listing.

2. The MFA protein as claimed in claim 1, wherein it specifically binds to N-acetylneuraminic acid or a glycoprotein including N-acetylneuraminic acid by hemagglutination reaction and hemagglutination-inhibition reaction.

3. A process for preparing a lectin MFA protein from the bark of the Korean plant *Maackia fauriei*, comprising the steps of: removing the outer coat from the bark of *Maackia fauriei*, homogenizing the bark and mixing the homogenate with an aqueous NaCl solution under stirring, filtering the precipitate with a filter, applying the filtrate onto column chromatography to give the crude fractions and further purifying the active fraction through a fetuin-affinity column to give the lectin MFA protein.

4. A diagnosing agent for a disease in which the structure of carbohydrates within the cells contains N-acetylneuraminic acid and its distribution is changed due to invasion of diseases, which comprises the lectin MFA according to claim 1 and said disease is selected from the group consisting of hepatoma, melanoma, choriocarcinoma, osteosarcoma and colon cancer.

5. A drug conjugate in which the lectin MFA protein according to claim 1 acts as a carrier protein for local transport of a drug and a selective drug as an active agent are bonded.

6. An anti-proliferation agent for cancer cells comprising the lectin MFA protein according to claim 1 as an active agent.

7. The anti-proliferation agent for cancer cells as claimed in claim 6, wherein the cancer cells are associated with breast cancer, melanoma or hepatoma.

* * * * *